(12) United States Patent
Hodges et al.

(10) Patent No.: US 6,632,349 B1
(45) Date of Patent: Oct. 14, 2003

(54) HEMOGLOBIN SENSOR

(75) Inventors: Alastair Hodges, San Diego, CA (US);
Ron Chatelier, San Diego, CA (US);
Thomas Beck, North Richmond (AU)

(73) Assignee: LifeScan, Inc., Milpitas, CA (US)

( * ) Notice: Subject to any disclaimer, the term of this patent is extended or adjusted under 35 U.S.C. 154(b) by 0 days.

(21) Appl. No.: 09/616,512

(22) Filed: Jul. 14, 2000

Related U.S. Application Data (63) Continuation-in-part of application No. 09/314,251, filed on May 18, 1999, now Pat. No. 6,174,420, which is a continuation of application No. 08/852,804, filed on May 7, 1997, now Pat. No. 5,942,102, and a continuation-in-part of application No. 08/068,828, filed on Mar. 15, 1999, now Pat. No. 6,179,979.

(30) Foreign Application Priority Data

Nov. 15, 1996 (WO) ................................ PCT/AU96/00724
Nov. 15, 1996 (WO) ................................ PCTAU9600723

(51) Int. Cl.$^7$ ............................................. G01N 27/327
(52) U.S. Cl. ............... 205/792; 205/777.5; 204/403.01; 204/403.02; 156/292
(58) Field of Search ................................ 204/400, 403, 204/409, 403.01, 403.02; 205/777.5, 778, 792; 156/292; 435/7.4, 817

(56) References Cited

U.S. PATENT DOCUMENTS

| | | |
|---|---|---|
| 3,552,928 A | 1/1971 | Fetter |
| 4,053,381 A | 10/1977 | Hamblen et al. |
| 4,076,596 A | 2/1978 | Connery et al. |
| 4,125,372 A | 11/1978 | Kawai et al. |
| 4,168,146 A | 9/1979 | Grubb et al. |
| 4,224,125 A | 9/1980 | Nakamura et al. |
| 4,225,557 A | 9/1980 | Hartl et al. |
| 4,301,412 A | 11/1981 | Hill et al. |
| 4,301,414 A | 11/1981 | Hill et al. |
| 4,319,969 A | 3/1982 | Oda et al. |

(List continued on next page.)

FOREIGN PATENT DOCUMENTS

| | | |
|---|---|---|
| AU | A-31042/93 | 7/1993 |
| AU | A-54873/94 | 8/1994 |

(List continued on next page.)

OTHER PUBLICATIONS

Bard and Faulkner, Electrochemical Methods: Fundamentals and Applications, 1980, pp. 22–26.*
International Search Report; PCT/US01/21964.
Abstract for JP 6310746 A; To: Miyahara et al.

*Primary Examiner*—Nam Nguyen
*Assistant Examiner*—Kaj K. Olsen
(74) *Attorney, Agent, or Firm*—Knobbe Martens Olson & Bear LLP (57) ABSTRACT

The present invention relates to a device and method for measuring hemoglobin in a fluid sample. The device comprises a disposable electrochemical cell, such as a thin layer electrochemical cell, containing a reagent capable of being reduced by hemoglobin. A suitable fluid sample that may be analyzed according the present invention is whole blood. If the hemoglobin to be analyzed is present in red blood cells, a lysing agent may be added to the sample to release the hemoglobin prior to analysis.

66 Claims, 1 Drawing Sheet

U.S. PATENT DOCUMENTS

| | | |
|---|---|---|
| 4,374,013 A | 2/1983 | Enfors |
| 4,404,066 A | 9/1983 | Johnson |
| 4,431,004 A | 2/1984 | Bessman et al. |
| 4,431,507 A | 2/1984 | Nankai et al. |
| 4,508,613 A | 4/1985 | Busta et al. |
| 4,508,821 A | 4/1985 | Mansour et al. |
| 4,517,287 A | 5/1985 | Scheibe et al. |
| 4,517,291 A | 5/1985 | Seago |
| 4,533,440 A | 8/1985 | Kim |
| 4,545,382 A | 10/1985 | Higgins et al. |
| 4,552,840 A | 11/1985 | Riffer |
| 4,604,264 A | 8/1986 | Rothe et al. |
| 4,637,978 A | 1/1987 | Dappen |
| 4,654,197 A | 3/1987 | Lilja et al. |
| 4,711,245 A | 12/1987 | Higgins et al. |
| 4,790,979 A | 12/1988 | Terminiello et al. |
| 4,797,256 A | 1/1989 | Watlington, IV |
| 4,820,489 A | 4/1989 | Rothe et al. |
| 4,871,258 A | 10/1989 | Herpichboehm et al. |
| 4,876,205 A * | 10/1989 | Green et al. .................. 422/98 |
| 4,883,764 A | 11/1989 | Kloepfer |
| 4,897,173 A | 1/1990 | Nankai et al. |
| 4,900,424 A | 2/1990 | Birth et al. |
| 4,919,770 A | 4/1990 | Preidel et al. |
| 4,943,522 A | 7/1990 | Eisinger et al. |
| 4,963,815 A | 10/1990 | Hafeman |
| 4,988,429 A | 1/1991 | Matthiessen |
| 4,994,238 A | 2/1991 | Daffern et al. |
| 5,059,908 A | 10/1991 | Mina |
| 5,096,809 A | 3/1992 | Chen et al. |
| 5,120,420 A | 6/1992 | Nankai et al. |
| 5,122,244 A | 6/1992 | Hoenes et al. |
| 5,126,034 A | 6/1992 | Carter et al. |
| 5,128,015 A | 7/1992 | Szuminsky et al. |
| 5,141,868 A | 8/1992 | Shanks et al. |
| 5,156,972 A | 10/1992 | Issachar |
| 5,179,005 A | 1/1993 | Phillips et al. |
| 5,185,256 A | 2/1993 | Nankai et al. |
| 5,192,415 A | 3/1993 | Yoshioka et al. |
| 5,229,282 A | 7/1993 | Yoshioka et al. |
| 5,272,087 A | 12/1993 | El Murr et al. |
| 5,306,623 A | 4/1994 | Kiser et al. |
| 5,312,590 A | 5/1994 | Gunasingham |
| 5,314,605 A | 5/1994 | Matthiessen |
| 5,320,732 A | 6/1994 | Nankai et al. |
| 5,382,346 A | 1/1995 | Uenoyama et al. |
| 5,384,028 A | 1/1995 | Ito |
| 5,385,846 A | 1/1995 | Kuhn et al. |
| 5,393,399 A | 2/1995 | Van den Berg et al. |
| 5,413,690 A | 5/1995 | Kost et al. |
| 5,418,142 A | 5/1995 | Kiser et al. |
| 5,437,999 A | 8/1995 | Diebold et al. |
| 5,508,171 A | 4/1996 | Walling et al. |
| 5,509,410 A | 4/1996 | Hill et al. |
| 5,518,590 A | 5/1996 | Fang |
| 5,567,302 A | 10/1996 | Song et al. |
| 5,628,890 A | 5/1997 | Carter et al. |
| 5,645,709 A | 7/1997 | Birch et al. |
| 5,776,324 A | 7/1998 | Usala |
| 5,863,400 A | 1/1999 | Drummond et al. |
| 5,942,102 A | 8/1999 | Hodges et al. |
| 5,997,817 A | 12/1999 | Crismore et al. |
| 6,054,039 A * | 4/2000 | Shieh .................... 204/403.06 |
| 6,111,096 A * | 8/2000 | Laugharn et al. .............. 203/1 |
| 6,251,260 B1 * | 6/2001 | Heller et al. ................. 204/402 |

FOREIGN PATENT DOCUMENTS

| | | |
|---|---|---|
| EP | 0 251 915 A2 | 1/1988 |
| EP | 0 255 291 A2 | 2/1988 |
| EP | 0 278 647 A2 | 8/1988 |
| EP | 0 345 781 A2 | 12/1989 |
| EP | 0 351 516 A2 | 1/1990 |
| EP | 0 400 918 A1 | 12/1990 |
| EP | 0 407 800 A2 | 1/1991 |
| EP | 0 415 679 A2 | 3/1991 |
| EP | 0 475 692 A1 | 3/1992 |
| EP | 0 479 394 A2 | 4/1992 |
| EP | 0 560 336 A1 | 9/1993 |
| EP | 0 574 134 A2 | 12/1993 |
| EP | 0 741 186 A2 | 11/1996 |
| EP | 0 764 469 A2 | 3/1997 |
| EP | 0 864 059 A2 | 12/1999 |
| GB | 2 201 248 A | 8/1988 |
| WO | WO 89/08713 | 9/1989 |
| WO | WO 92/15701 | 9/1992 |
| WO | WO 95/16198 | 6/1995 |
| WO | WO 95/21934 | 8/1995 |
| WO | WO 95/28634 | 10/1995 |
| WO | WO 97/00441 | 1/1997 |
| WO | WO 97/18464 | 5/1997 |
| WO | 97/18465 | 5/1997 |
| WO | WO 98/11426 | 3/1998 |
| WO | WO 98/43073 | 10/1998 |
| WO | WO 98/43074 | 10/1998 |
| WO | WO 99/46585 | 9/1999 |
| WO | 99/62918 | 12/1999 |

* cited by examiner

HEMOGLOBIN SENSOR

RELATED APPLICATIONS

This application is a continuation-in-part of copending application Ser. No. 09/314,251, filed May 18, 1999, now U.S. Pat. No. 6,174,420. Application Ser. No. 09/314,251 is a continuation of application Ser. No. 08/852,804, filed May 7, 1997, now U.S. Pat. No. 5,942,102, and a continuation of application Ser. No. 08/068,828, filed Mar. 15, 1999, now U.S. Pat. No. 6,179,979. Application Ser. No. 08/852,804 is the national phase under 35 U.S.C. §371 of prior PCT International Application No. PCT/AU96/00723 which has an International filing date of Nov. 15, 1996, which designated the United States of America, and which was published by the International Bureau in English on May 22, 1997, and claims the benefit of Australian Provisional Patent Application No. PN 6619, filed Nov. 16, 1995. Application Ser. No. 08/068,828 is the national phase under 35 U.S.C. §371 of prior PCT international Application No. PCT/AU96/00724 which has an International filing date of Nov. 15, 1996, which designated the United States of America, and which was published by the International Bureau in English on May 22, 1997, and claims the benefit of Australian Provisional Patent Application No. PN 6619, filed Nov. 16, 1995.

FIELD OF THE INVENTION

The present invention relates to a device and method for measuring the level of hemoglobin in a blood sample. The device comprises a disposable electrochemical cell containing an agent which lyses red blood cells and a reagent capable of being reduced by hemoglobin.

BACKGROUND OF THE INVENTION

Hemoglobin is a respiratory molecule found in red blood cells. It is responsible for transporting oxygen from the lungs to body cells and for transporting carbon dioxide from body cells to the lungs. Hemoglobin has a molecular weight of 68,000 and contains four polypeptide chains. Each chain binds to a heme group which consists of a tetrapyrrole ring chelated to an $Fe^{+2}$ ion. In the lungs, the iron atoms of the hemoglobin molecule reversibly combine with an oxygen molecule, which is then transported to body cells as blood circulates. The oxygen is released from the hemoglobin molecule in the tissues, then the oxygen-free hemoglobin molecule picks up carbon dioxide which is transported back to the lungs, where it is released.

Hemoglobin is produced in cells in the bone marrow that become red blood cells. Certain illnesses result in a deficiency of hemoglobin, such as anemia and sickle cell disease. Still other diseases, such as polycythemia or erythrocytosis, result in excessive levels of hemoglobin. Therefore, as an aid in the diagnosis or monitoring of such diseases, a method and device for determining the concentration of hemoglobin in whole blood is desirable.

Numerous methods and devices for the determination of hemoglobin are known. These methods include both direct analysis, i.e., analysis without prior modification of the hemoglobin, and indirect analysis. An example of a direct analysis method is the Tallquist Method, wherein a measurement of the transmission or reflection optical density of the red color imparted by oxyhemoglobin, one form of hemoglobin, is obtained. An example of an indirect analysis method is Drabkin's Method. In this method, the iron in hemoglobin is oxidized with a ferricyanide to form methemoglobin, which is converted with a cyanide to cyanmethemoglobin, which is then measured spectrometrically. Both of these methods have the disadvantage of requiring expensive analytical instrumentation and complicated sample preparation. Therefore, a quick, simple, and inexpensive device and method for measuring hemoglobin that overcomes the deficiencies of prior art methods is desirable.

SUMMARY OF THE INVENTION

The present invention provides a device and method for measuring hemoglobin with a disposable sensing element, suitable for a single use, that can be combined with a meter to give a robust, fast, and easy to use test that is amenable to field as well as laboratory use. In particular, the invention relates to the use of an electrochemical sensor that utilizes a redox agent that reacts with hemoglobin to produce an electrochemically detectable signal. The method of the present invention measures total hemoglobin, oxygenated plus unoxygenated, in contrast to spectrophotometric methods wherein the hemoglobin must be converted to a single form in a separate chemical step, e.g., oxidation of hemoglobin containing $Fe^{+2}$ to methemoglobin containing $Fe^{+3}$. Measurement of hemoglobin by the method of the present invention is not dependent upon the extent of glycosylation or oxygenation of the hemoglobin present in the sample.

In a first aspect of the present invention, a device for detecting a presence or an absence of hemoglobin in an aqueous sample is provided, the device including an electrochemical cell having a sensing chamber, a first electrode, a second electrode, an aperture for admitting the sample into the sensing chamber, and a reagent contained within the sensing chamber wherein the reagent is capable of being reduced by hemoglobin to generate an electrical signal indicative of the presence or absence of hemoglobin. The electrochemical cell may be designed to be disposed of after use in a single experiment.

In one aspect of this embodiment, first electrode is a sensing electrode. The sensing electrode may be platinum, palladium, carbon, indium oxide, tin oxide, gold, iridium, copper, steel, silver, or mixtures thereof The first electrode may be formed by a technique including sputtering, vapor coating, screen printing, thermal evaporation, ink jet printing, ultrasonic spraying, slot coating, gravure printing or lithography.

In another aspect of this embodiment, the second electrode is a counter electrode. The second electrode may be a metal in contact with a metal salt, for example, silver in contact with silver chloride, silver in contact with silver bromide, silver in contact with silver iodide, mercury in contact with mercurous chloride, and mercury in contact with mercurous sulfate. The second electrode may also be a reference electrode.

In another aspect of this embodiment, the electrochemical cell further includes a third electrode, which may be a reference electrode. The third electrode may include a metal in contact with a metal salt, for example, silver in contact with silver chloride, silver in contact with silver bromide, silver in contact with silver iodide, mercury in contact with mercurous chloride, and mercury in contact with mercurous sulfate.

In another aspect of this embodiment, the reagent may include dichromate, vanadium oxides, permanganate, electroactive organometallic complexes, quinones, dichlorophenolindophenol, and ferricyanide. A buffer, such as a phosphate, carbonate, alkali metal salt of mellitic acid, or alkali metal salt of citric acid, may be contained within the sensing chamber. The sensing chamber further includes a red blood cell lysing agent, for example, one selected from ionic detergents, nonionic detergents, proteolytic enzymes, lipases, saponin, sodium dodecyl sulfate, cetyl trimethylammonium bromide, or polyethoxylated octylphenol.

In another aspect of this embodiment, the sample includes whole blood.

In another aspect of this embodiment, the sensing chamber further includes a support contained within the sensing chamber, for example, mesh, nonwoven sheet, fibrous filler, macroporous membrane, sintered powder, or combinations thereof. The reagent, red blood cell lysing agent, and/or buffer may be contained within or supported on the support.

In another aspect of this embodiment, the second electrode is mounted in opposing relationship a distance of less than about 500 microns from the first electrode; less than about 150 microns from the first electrode; or less than about 150 microns and greater than about 50 microns from the first electrode.

In another aspect of this embodiment, the device includes an interface for communication with a meter. The interface may communicate a voltage or a current. The electrochemical cell may be a thin layer electrochemical cell.

In a second aspect of the present invention, a method for detecting a presence or an absence of hemoglobin in an aqueous sample is provided, the method including providing a device including an electrochemical cell having a sensing chamber, a first electrode, a second electrode, an aperture for admitting the sample into the sensing chamber, and a reagent contained within the sensing chamber, wherein the reagent is capable of being reduced by hemoglobin to generate an electrical signal indicative of the presence or absence of hemoglobin; providing an aqueous sample; allowing the sample to flow through the aperture and into the sensing chamber, such that the first and second electrodes are substantially covered; and obtaining an electrochemical measurement indicative of the presence or absence of hemoglobin present in the sample.

In one aspect of this embodiment, the electrochemical cell is designed to be disposed of after use in a single experiment, or may be a thin layer electrochemical cell. The electrochemical measurement may be an amperometric measurement, a potentiometric measurement, a coulometric measurement, or a quantitative measurement.

In a third aspect of the present invention, a method is provided for measuring hemoglobin in a fluid whole blood sample, the whole blood sample containing red blood cells, the red blood cells containing hemoglobin, wherein the method includes providing a device including an electrochemical cell having a sensing chamber, a first electrode, a second electrode, an aperture for admitting the sample into the sensing chamber; a reagent contained within the sensing chamber and capable of being reduced by hemoglobin; and a red blood cell lysing agent contained within the sensing chamber; placing the whole blood sample in the sensing chamber, whereby the lysing agent contained within the sensing chamber releases hemoglobin from the red blood cells, whereby the hemoglobin thus released reduces the reagent; and obtaining an electrochemical measurement indicative of the level of hemoglobin present in the whole blood sample.

In one aspect of this embodiment, the electrochemical cell is designed to be disposed of after use in a single experiment, or may be a thin layer electrochemical cell.

In one aspect of this embodiment, the method further includes obtaining an electrochemical measurement indicative of the presence or absence of hemoglobin in the sample by applying a negative potential to the first electrode; measuring a current generated by reaction of the reagent and hemoglobin; analyzing the current to give a result, the result including a time required for substantial lysis of the red blood cells or a derived final value for the current; calculating a percentage of the reaction completed as a function of time based on the result of the analyzing step; reversing the potential on the first electrode; measuring a transient current; and determining a diffusion coefficient and a concentration of a reduced form of the reagent based on the transient current.

In a fourth aspect of the present invention, a method of manufacture of a device for detecting the presence or absence of hemoglobin in an aqueous sample is provided, the device including an electrochemical cell having a sensing chamber, a first electrode, a second electrode, an aperture for admitting the sample into the sensing chamber, and a reagent contained within the sensing chamber, and wherein the reagent is capable of being reduced by hemoglobin to generate an electrical signal indicative of the presence or absence of hemoglobin, the method including forming an aperture extending through a sheet of electrically resistive material, the aperture defining a side wall of the sensing chamber; mounting a first layer having a first electrode to a first side of the sheet and extending over the aperture whereby to define a first sensing chamber end wall, the first electrode facing the first side of the sheet; mounting a second layer having a second electrode to a second side of the sheet and extending over the aperture whereby to define a second sensing chamber end wall in substantial overlying registration with the first layer, the second electrode facing the second side of the sheet, whereby the sheet and layers form a strip; providing an aperture in the strip to permit entry of sample into the sensing chamber; and providing a reagent capable of being reduced by hemoglobin, wherein the reagent is contained within the sensing chamber.

In one aspect of this embodiment, the method further includes the step of providing a vent in the strip to permit the escape of air displaced from the sensing chamber as sample fills the sensing chamber.

In another aspect of this embodiment, the aperture is of a rectangular cross-section.

In another aspect of this embodiment, at least one of the electrodes includes a noble metal, such as palladium, platinum, and silver. At least one of the electrodes may be a sputter coated metal deposit. The electrodes may be adhered to the sheet, for example, by an adhesive such as a heat activated adhesive, pressure sensitive adhesive, heat cured adhesive, chemically cured adhesive, hot melt adhesive, and hot flow adhesive.

In another aspect of this embodiment, the method may include the step of providing a buffer and/or a red blood cell lysing agent contained within the sensing chamber. The reagent and/or buffer may be printed onto at least one wall of the sensing chamber. A support contained within the sensing chamber may also be provided, such as mesh, fibrous filler, macroporous membrane, sintered powder, or combinations thereof. The reagent may be supported on or contained within the support.

In another aspect of this embodiment, at least the sheet or one of the layers includes a polymeric material selected from polyester, polystyrene, polycarbonate, polyolefin, and mixtures thereof, or polyethylene terephthalate.

In another aspect of this embodiment, the second electrode is mounted in opposing relationship a distance of less than about 500 microns from the first electrode; less than about 150 microns from the first electrode; or less than about 150 microns and greater than about 50 microns from the first electrode.

In another aspect of this embodiment, the electrochemical cell is designed to be disposed of after use in a single experiment.

DETAILED DESCRIPTION OF THE PREFERRED EMBODIMENTS

The following description and examples illustrate a preferred embodiment of the present invention in detail. Those of skill in the art will recognize that there are numerous variations and modifications of this invention that are encompassed by its scope. Accordingly, the description of a preferred embodiment should not be deemed to limit the scope of the present invention.

Other methods and devices for obtaining electrochemical measurements of fluid samples are discussed further in copending U.S. patent application Ser. No. 09/616,433, filed on Jul. 14, 2000, entitled "IMMUNOSENSOR," copending U.S. patent application Ser. No. 09/615,691, filed on Jul. 14, 2000, allowed entitled "ANTIOXIDANT SENSOR," and copending U.S. patent application Ser. No. 09/616,556, filed on Jul. 14, 2000, now U.S. Pat. No. 6,444,115 entitled "ELECTROCHEMICAL METHOD FOR MEASURING CHEMICAL REACTION RATES," each of which is incorporated herein by reference in its entirety.

The Sample

In preferred embodiments, a method and device for measuring hemoglobin levels in a fluid whole blood sample is provided. If the whole blood sample is not in liquid form, i.e., dried blood, it can be analyzed after solid sample is mixed into a suitable fluid, e.g., water. Whole blood contained within a solid tissue sample may be analyzed after extraction using techniques well-known in the art.

Prior to its analysis, hemoglobin must be released from the red blood cells in which it is contained. This may be accomplished by pretreating the whole blood sample with a lysing agent prior to its introduction into the electrochemical cell. Alternatively, a lysing agent may be contained within the electrochemical cell itself. Other agents may also be used to pretreat the sample. For example, pH may be adjusted to a desired level by means of a buffer or neutralizing agent, or a substance that renders interfering species nonreactive may be added.

The Electrochemical Cell

Figure 1:
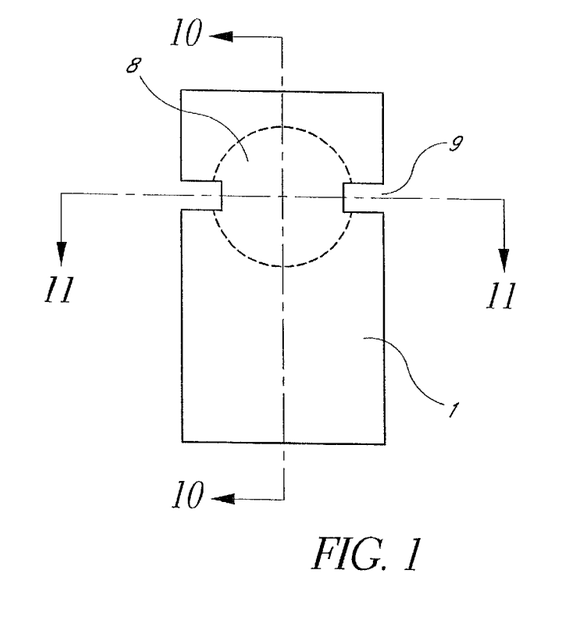
FIG. 1 shows a plan view of an electrochemical cell.
Figure 2:
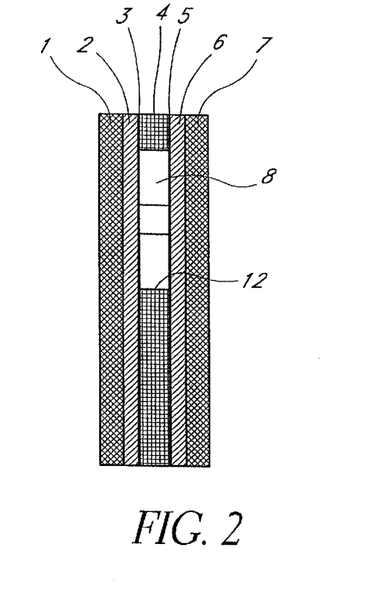
FIG. 2 shows a cross-section view on line 10—10 of FIG. 1.
Figure 3:
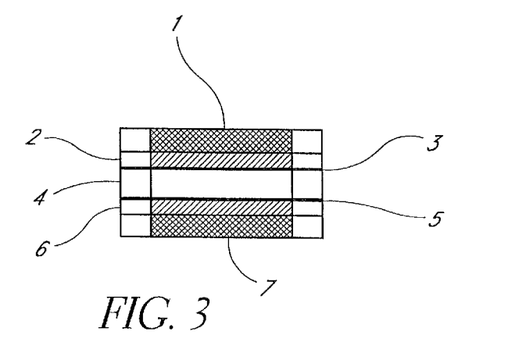
FIG. 3 shows an end-section view on line 11—11 of FIG. 1.

The electrochemical cell of present invention is disposable and designed for use in a single experiment. In a preferred embodiment, the electrochemical cell is a thin layer sensor such as that disclosed in U.S. Pat. No. 5,942,102 (incorporated herein by reference in its entirety). As herein used, the term "thin layer electrochemical cell" refers to a cell having closely spaced electrodes such that reaction products from the counter electrode arrive at the working electrode. In practice, the separation of electrodes in such a cell for measuring glucose in blood will be less than 500 microns, and preferably less than 200 microns. A preferred embodiment of such an electrochemical cell is illustrated in FIGS. 1, 2, and 3. The cell illustrated in FIGS. 1, 2, and 3 includes a polyester core 4 having a circular aperture 8. Aperture 8 defines a cylindrical cell side wall 12. Adhered to one side of core 4 is a polyester sheet 1 having a sputter coating of palladium 2. The sheet is adhered by means of an adhesive 3 to core 4 with palladium 2 adjacent core 4 and covering aperture 8. A second polyester sheet 7 having a second sputter coating of palladium 6 is adhered by means of contact adhesive 5 to the other side of core 4 and covering aperture 8. There is thereby defined a cell having cylindrical side wall 12 closed on each end by palladium metal 2, 6. The assembly is notched at 9 to provide for a solution to be admitted to the cell or to be drawn in by wicking or capillary action and to allow air to escape. The metal films 2, 6 are connected with suitable electrical connections or formations whereby potentials may be applied and currently measured.

Such a thin layer electrochemical cell is prepared by first forming an aperture extending through a sheet of electrically resistive material, the aperture defining a side wall of the electrochemical cell. Suitable electrically resistive materials, which may be used in the sheet containing the aperture, or in other layers in the cell, include, for example, materials such as polyesters, polystyrenes, polycarbonates, polyolefins, polyethylene terephthalate, mixtures thereof, and the like. In a preferred embodiment, the aperture in the sheet is rectangular, however other shapes, e.g., circular, may be used as well.

After the aperture is formed, a first thin electrode layer is then mounted on one side of the sheet of electrically resistive material, extending over the aperture and forming an end wall. The layer may be adhered to the sheet, for example, by means of an adhesive. Suitable adhesives include, for example, heat activated adhesives, pressure sensitive adhesives, heat cured adhesives, chemically cured adhesives, hot melt adhesives, hot flow adhesives, and the like. The electrode layer is prepared by coating (e.g., by sputter coating) a sheet of electrically resistive material with a suitable metal, for example, palladium.

A second thin electrode layer is then mounted on the opposite side of the electrically resistive material, also extending over the aperture, so as to form a second end wall. In a preferred embodiment, the electrode layers are mounted in opposing relationship at a distance of less than about 1 millimeter, desirably less than about 800 microns, more desirably less that about 600, or preferably less than about 500 microns, more preferably less than about 300 to 150 microns, more preferably less than 150 microns, and most preferably between 25, 40, 50, 100 and 150 microns. A second aperture or ingress is then provided for liquid to enter the cell. Such an ingress can be provided by forming a notch along one edge of the device which extends through the electrode layers and aperture. The electrode layers are provided with connection means allowing the sensors to be placed in a measuring circuit.

Chemicals for use in the cell, such as redox reagents, lysing agents, buffers, and other substances, may be supported on the cell electrodes or walls, on one or more independent supports contained within cell, or may be self supporting. If the chemicals are to be supported on the cell electrodes or walls, the chemicals may be applied by use of application techniques well known in the art, such as ink jet printing, screen printing, lithography, ultrasonic spraying, slot coating, gravure printing, and the like. Suitable independent supports may include, but are not limited to, meshes, nonwoven sheets, fibrous fillers, macroporous membranes, and sintered powders. The chemicals for use in the cell may be supported on or contained within a support.

In a preferred embodiment, the materials used within the cell as well as the materials used to construct the cell are in a form amenable to mass production, and the cells themselves are designed to be able to be used for a single experiment then disposed of.

According to the present invention a disposable cell is one that is inexpensive enough to produce that it is economically acceptable to be used only for a single test. Secondly, that the cell may conveniently only be used for a single test. Inconveniently in this context means that steps such as washing and/or reloading of reagents would need to be taken to process the cell after a single use to render it suitable for a subsequent use.

Economically acceptable in this context means that the perceived value of the result of the test to the user is the same or greater than the cost of the cell to purchase and use, the cell purchase price being set by the cost of supplying the cell to the user plus an appropriate mark up. For many applications, this requires that the cells have relatively low materials costs and simple fabrication processes. For example, the electrode materials of the cells should be inexpensive, such as carbon, or be used in sufficiently small amounts such that expensive materials may be used. Screen printing carbon or silver ink is a process suitable for forming electrodes with relatively inexpensive materials. However, if it is desired to use electrode materials such as platinum, palladium, gold or iridium, methods with better material utilization, such as sputtering or evaporative vapor coating, are more suitable as they may give extremely thin films. The substrate materials for the disposable cells also need to be inexpensive. Examples of such inexpensive materials are polymers such as polyvinylchloride, polyimide, polyester and coated papers and cardboard.

Cell assembly methods also need to be amenable to mass production. These methods include fabricating multiple cells on cards and separating the card into individual strips subsequent to the main assembly steps, and web fabrication where the cells are produced on a continuous web, which is subsequently separated into individual strips. Card processes are most suitable when close spatial registration of multiple features is required for the fabrication and/or when stiff cell substrate materials are to be used. Web processes are most suitable when the down web registration of features is not as critical and flexible webs may be used.

The convenient single use requirement for the disposable cell is desirable so that users are not tempted to try to reuse the cell and possibly obtain an inaccurate test result. The single use requirement for the cell may be stated in user instructions accompanying the cell. More preferably, the cell may also be fabricated such that using the cell more than once is difficult or not possible. This may be accomplished, for example, by including reagents that are washed away or consumed during the first test and so are not functional in a second test. Alternatively, the signal of the test may be examined for indications that reagents in the cell have already reacted, such as an abnormally high initial signal, and the test aborted. Another method includes providing a means for breaking electrical connections in the cell after the first test in a cell has been completed.

The Electrodes

At least one of the electrodes in the cell is a sensing electrode, defined as an electrode sensitive to the amount of oxidized redox agent. In the case of a potentiometric sensor wherein the potential of the sensing electrode is indicative of the level of hemoglobin present, a second electrode acting as reference electrode is present which acts to provide a reference potential.

In the case of an amperometric sensor wherein the sensing electrode current is indicative of the level of hemoglobin in the sample, at least one other electrode is present which functions as a counter electrode to complete the electrical circuit. This second electrode may also function as a reference electrode. Alternatively, a separate electrode may perform the function of a reference electrode.

Materials suitable for the sensing, counter, and reference electrodes must be compatible with the redox reagents present in the device. Compatible materials will not react chemically with the redox reagent or any other substance present in the cell. Examples of such suitable materials include, but are not limited to, platinum, palladium, carbon, indium oxide, tin oxide, mixed indium/tin oxides, gold, silver, iridium and mixtures thereof. These materials may be formed into electrode structures by any suitable method, for example, by sputtering, vapor coating, screen printing, thermal evaporation or lithography. In preferred embodiments, the material is sputtered or screen printed to form the electrode structures.

Non-limiting examples of materials suitable for use in the reference electrode include metal/metal salt systems such as silver in contact with silver chloride, silver bromide or silver iodide, and mercury in contact mercurous chloride or mercurous sulfate. The metal may be deposited by any suitable method and then brought into contact with the appropriate metal salt. Suitable methods include, for example, electrolysis in a suitable salt solution or chemical oxidation. Such metal/metal salt systems provide better potential control in potentiometric measurement methods than do single metal component systems. In a preferred embodiment, the metal/metal salt electrode systems are used as a separate reference electrode in an amperometric sensor.

The Lysing Agent

Suitable red blood cell lysing agents include detergents, both ionic and nonionic, proteolytic enzymes, and lipases. Suitable ionic detergents include, for example, sodium dodecyl sulfate and cetyl trimethylammonium bromide. Non-limiting examples of proteolytic enzymes include trypsin, chymotrypsin, pepsin, papain, and Pronase E, a very active enzyme having broad specificity. Nonionic surfactants suitable for use include, e.g., ethoxylated octylphenols, including the Triton X Series available from Rohm & Haas of Philadelphia, Pa. In a preferred embodiment, saponins, i.e., plant glycosides that foam in water, are used as the lysing agent.

The Redox Reagent

Suitable redox reagents include those which are capable of oxidizing hemoglobin. Examples of redox reagents suitable for use in analyzing hemoglobin include, but are not limited, to salts of ferricyanide, dichromate, vanadium oxides, permanganate, and electroactive organometallic complexes. Organic redox reagents such as dichlorophenolindophenol, and quinones are also suitable. In a preferred embodiment, the redox reagent for analyzing hemoglobin is ferricyanide.

The Buffer

Optionally, a buffer may be present along with the redox reagent in dried form in the electrochemical cell. If a buffer is used, it is present in an amount such that the resulting pH level is suitable for adjusting the oxidizing potential of the redox reagent to a level suitable for oxidizing hemoglobin but not other species that it is not desired to detect. The buffer is present in a sufficient amount so as to substantially maintain the pH of the sample at the desired level during the test. Examples of buffers suitable for use include phosphates, carbonates, alkali metal salts of mellitic acid, and alkali metal salts of citric acid. The choice of buffer will depend on the desired pH. The buffer is selected so as not to react with the redox reagent.

Other Substances Present Within The Cell

In addition to redox reagents and buffers, other substances may also be present within the electrochemical cell. Such substances include, for example, viscosity enhancers and low molecular weight polymers. Hydrophilic substances may also be contained within the cell, such as polyethylene glycol, polyacrylic acid, dextran, and surfactants such as those marketed by Rohm & Haas Cormpany of Philadelphia, Pa., under the trade name Triton™ or by ICI Americas Inc. of. Wilmington, Del., under the trade name Tween™. Such substances may enhance the fill rate of the cell, provide a more stable measurement, and inhibit evaporation in small volume samples.

Method for Measuring Hemoglobin Concentration

In measuring hemoglobin present in a whole blood sample, the sample is introduced into the sensor cell, whereupon the sample dissolves the dried reagents and other substances present in the sensor cell. If the sample has not been pretreated with a lysing agent, a lysing agent present in the sensor cell releases hemoglobin from the red blood cells. The redox reagent then reacts with hemoglobin present in the sample to form the reduced form of the redox reagent. In the case of a potentiometric sensor, the resulting ratio of oxidized to reduced form of the redox reagent fixes the potential of the sensing electrode relative to the reference electrode. This potential is then used as a measure of the concentration of the hemoglobin originally in the sample.

In a preferred embodiment, the sensing cell is operated as an amperometric sensor. According to this embodiment, the reduced redox reagent formed by reaction with hemoglobin is electrochemically oxidized at the sensing electrode. The current resulting from this electrochemical reaction is then used to measure the concentration of hemoglobin originally in the sample. In other embodiments, the sensor is operated in potentiometric or coulometric mode.

The cell's electrodes are used to produce an electrical signal, i.e., a voltage or current, readable by an attached meter. In a preferred embodiment, an interface for connecting the cell to the meter is provided. The meter may display the measurement in a visual, audio or other form, or may store the measurement in electronic form.

In a preferred embodiment where ferricyanide is used as the reagent, a typical concentration of hemoglobin, e.g., 14 g/dL, would yield a ferrocyanide concentration of 8.2 mM upon oxidation. The minimum detectable limit in a preferred embodiment of the method and device is approximately 0.1 mM.

Measuring Hemoglobin Using First and Second Potential Application Steps

In a preferred embodiment, substantially complete lysis of all red blood cells is achieved before measurement of hemoglobin. However, a rapid hemoglobin measurement may be obtained even if the lysis step proceeds slowly by using a first and second potential application step.

In such an embodiment, a sensor configuration as described above is used, e.g., a sensor wherein the bottom electrode is palladium, upon which the dried reagents are deposited, and wherein the top electrode is a gold electrode. The first potential is applied by applying a −0.3 V potential at zero time to set the gold electrode as the working electrode. As the red blood cells begin to lyse and the ferricyanide reacts with released hemoglobin, the current will slowly increase. The increase in current can be used in a number of ways: to assess the time required for full lysis and reaction, to extrapolate the signal to longer times, or to assess the fraction of hemoglobin reacted at a given time. The first method gives some quality assurance, and the second and third methods yield a shorter test.

After the first potential has been applied and current has been measured, the potential can be reversed to +0.3 V and the reverse transient current can be measured and analyzed using electrochemical methods known in the art, e.g., as disclosed in U.S. application Ser. No. 08/981385 filed Apr. 17, 1998, and U.S. Pat. No. 5,942,102 (both incorporated herein by reference in their entirety), to calculate the diffusion coefficient and concentration of ferrocyanide.

The first potential application may also be used to subtract interferents. The ferricyanide reacts more quickly with interfering substances which are free in the plasma than with hemoglobin which is packaged in red blood cells. The ratio of the minimum to maximum (or extrapolated) currents resulting from the first potential application may be used to yield the concentration of reduced mediator measured by the second potential pulse (at +0.3 V), thereby yielding a more accurate, corrected concentration of hemoglobin. The simplest correction would be:

$$[Hb]' = [Hb] * (1 - i_{min}/i_{max})$$

wherein [Hb]' is the corrected concentration of hemoglobin, [Hb] is the uncorrected concentration of hemoglobin, imin is the measured current and imax is the extrapolated current resulting from the first potential application.

The above description discloses several methods and materials of the present invention. This invention is susceptible to modifications in the methods and materials, as well as alterations in the fabrication methods and equipment. Such modifications will become apparent to those skilled in the art from a consideration of this disclosure or practice of the invention disclosed herein. Consequently, it is not intended that this invention be limited to the specific embodiments disclosed herein, but that it cover all modifications and alternatives coming within the true scope and spirit of the invention as embodied in the attached claims.

What is claimed is:

1. A device for measuring an amount of hemoglobin in a fluid whole blood sample, the whole blood sample containing red blood cells, the red blood cells containing hemoglobin, the device comprising an electrochemical cell having a sensing chamber, a first electrode, a second electrode wherein the second electrode is mounted in opposing relationship a distance of less than about 500 microns from the first electrode, an aperture for admitting the sample into the sensing chamber, a red blood cell lysing agent, and a reagent contained within the sensing chamber wherein the reagent is capable of being reduced by hemoglobin to generate an electrical signal indicative of the amount of hemoglobin, wherein the device further comprises means for applying a positive potential to the first electrode; means for measuring a current generated by reaction of the reagent and hemoglobin; means for analyzing the current to give a result, the result comprising a time required for substantial lysis of the red blood cells or a derived final value for the current; means for calculating a percentage of the reaction completed as a function of time based on the result of the analyzing step; means for reversing the potential on the first electrode; means for measuring a transient current; and means for determining a diffusion coefficient and a concentration of a reduced form of the reagent based on the transient current.

2. The device of claim 1, wherein the device may only be used for a single test.

3. The device of claim 1, wherein the first electrode comprises a sensing electrode.

4. The device of claim 1, wherein the first electrode comprises a material selected from the group consisting of platinum, palladium, carbon, indium oxide, tin oxide, gold, iridium, copper, steel, silver, and mixtures thereof.

5. The device of claim 1, wherein the first electrode is formed by a technique selected from the group consisting of sputtering, vapor coating, screen printing, thermal evaporation, ink jet printing, ultrasonic spraying, slot coating, gravure printing and lithography.

6. The device of claim 1, wherein the second electrode comprises a counter electrode.

7. The device of claim 1, wherein the second electrode comprises a metal in contact with a metal salt.

8. The device of claim 7, wherein the metal in contact with a metal salt is selected from the group consisting of silver in contact with silver chloride, silver in contact with silver bromide, silver in contact with silver iodide, mercury in contact with mercurous chloride, and mercury in contact with mercurous sulfate.

9. The device of claim 7, the electrochemical cell further comprising a third electrode.

10. The device of claim 9, wherein the third electrode comprises a reference electrode.

11. The device of claim 10, wherein the third electrode comprises a metal in contact with a metal salt.

12. The device of claim 11, wherein the metal in contact with the metal salt is selected from the group consisting of silver in contact with silver chloride, silver in contact with silver bromide, silver in contact with silver iodide, mercury in contact with mercurous chloride, and mercury in contact with mercurous sulfate.

13. The device of claim 1, wherein the second electrode comprises a reference electrode.

14. The device of claim 1, wherein the reagent is selected from the group consisting of dichromate, vanadium oxides, permanganate, electroactive organometallic complexes, quinones, and dichlorophenolindophenol.

15. The device of claim 1, wherein the reagent comprises ferricyanide.

16. The device of claim 1, the sensing chamber further comprising a buffer, wherein the buffer is contained within the sensing chamber.

17. The device of claim 16, wherein the buffer is selected from the group consisting of phosphates, carbonates, alkali metal salts of mellitic acid, and alkali metal salts of citric acid.

18. The device of claim 1, wherein the lysing agent is selected from the group consisting of ionic detergents, nonionic detergents, proteolytic enzymes, and lipases.

19. The device of claim 1, wherein the lysing agent comprises saponin.

20. The device of claim 1, wherein the lysing agent is selected from the group consisting of sodium dodecyl sulfate, cetyl trimethylammonium bromide, and polyethoxylated octylphenol.

21. The device of claim 1, the sensing chamber further comprising a support, the support contained within the sensing chamber.

22. The device of claim 21, wherein the support is a material selected from the group consisting of mesh, nonwoven sheet, fibrous filler, macroporous membrane, sintered powder, and combinations thereof.

23. The device of claim 21, wherein the reagent is contained within or supported on the support.

24. The device of claim 21, further comprising a buffer, wherein the buffer is contained within or supported on the support.

25. The device of claim 21, wherein the lysing agent is contained within or supported on the support.

26. The device of claim 1, wherein the second electrode is mounted in opposing relationship a distance of less than about 150 microns from the first electrode.

27. The device according to claim 1, wherein the second electrode is mounted in opposing relationship a distance of less than about 150 microns and greater than about 50 microns from the first electrode.

28. The device of claim 1, further comprising an interface for communication with a meter.

29. The device of claim 28, wherein the interface communicates a voltage or a current.

30. The device of claim 1, wherein the electrochemical cell comprises a thin layer electrochemical cell.

31. A method for measuring an amount of hemoglobin in a fluid whole blood sample, the whole blood sample containing red blood cells, the red blood cells containing hemoglobin, wherein the method comprises:

providing a device comprising an electrochemical cell having a sensing chamber, a first electrode, a second electrode wherein the second electrode is mounted in opposing relationship a distance of less than about 500 microns from the first electrode, an aperture for admitting the sample into the sensing chamber; a reagent contained within the sensing chamber and capable of being reduced by hemoglobin; and a red blood cell lysing agent contained within the sensing chamber;

placing the whole blood sample in the sensing chamber, whereby the lysing agent contained within the sensing chamber releases hemoglobin from the red blood cells, whereby the hemoglobin thus released reduces the reagent; and obtaining an electrochemical measurement indicative of an amount of hemoglobin present in the whole blood sample, wherein the step of obtaining an electrochemical measurement comprises:

applying a positive potential to the first electrode;

measuring a current generated by reaction of the reagent and hemoglobin;

analyzing the current to give a result, the result comprising a time required for substantial lysis of the red blood cells or a derived final value for the current;

calculating a percentage of the reaction completed as a function of time based on the result of the analyzing step;

reversing the potential on the first electrode;

measuring a transient current; and determining a diffusion coefficient and a concentration of a reduced form of the reagent based on the transient current.

32. The method of claim 31, wherein the device may only be used for a single test.

33. The method of claim 31, wherein the electrochemical cell is a thin layer electrochemical cell.

34. The method of claim 31, wherein the first electrode comprises a sensing electrode, the sensing electrode comprising a material selected from the group consisting of platinum, palladium, carbon, indium oxide, tin oxide, gold, iridium, copper, steel, silver, and mixtures thereof.

35. The method of claim 31, wherein the second electrode comprises a counter electrode, the counter electrode comprising a metal in contact with a metal salt.

36. The method of claim 35, wherein the metal in contact with a metal salt is selected from the group consisting of silver in contact with silver chloride, silver in contact with silver bromide, silver in contact with silver iodide, mercury in contact with mercurous chloride, and mercury in contact with mercurous sulfate.

37. The method of claim 31, the electrochemical cell further comprising a third electrode, the third electrode comprising a reference electrode.

38. The method of claim 31, wherein the reagent is selected from the group consisting of dichromate, vanadium oxides, permanganate, electroactive organometallic complexes, quinones, dichlorophenolindophenol, and ferricyanide.

39. The method of claim 31, the sensing chamber further comprising a buffer, wherein the buffer is contained within the sensing chamber.

40. The method of claim 39, wherein the buffer is selected from the group consisting of phosphates, carbonates, alkali metal salts of mellitic acid, and alkali metal salts of citric acid.

41. The method of claim 31, wherein the lysing agent is selected from the group consisting of ionic detergents, nonionic detergents, proteolytic enzymes, lipases, saponin, sodium dodecyl sulfate, cetyl trimethylanmmonium bromide, and polyethoxylated octylphenol.

42. The method of claim 31, the sensing chamber further comprising a support, the support contained within the sensing chamber.

43. The method of claim 31, wherein the second electrode is mounted in opposing relationship a distance of less than about 150 microns from the first electrode.

44. The method of claim 31, wherein the second electrode is mounted in opposing relationship a distance of less than about 150 microns and greater than about 50 microns from the first electrode.

45. The method of claim 31, wherein the electrochemical cell comprises a thin layer electrochemical cell.

46. A method of manufacture of a device for determining an amount of hemoglobin in a fluid whole blood sample, the whole blood sample comprising red blood cells, the red blood cells comprising hemoglobin, the device comprising an electrochemical cell having a sensing chamber, a first electrode, a second electrode, an aperture for admitting the sample into the sensing chamber, a red blood cell lysing agent, and a reagent contained within the sensing chamber, wherein the reagent is capable of being reduced by hemoglobin to generate an electrical signal indicative of the amount of hemoglobin in the sample, the method comprising:

forming an aperture extending through a sheet of electrically resistive material, the aperture defining a side wall of the sensing chamber;

mounting a first layer having a first electrode to a first side of the sheet and extending over the aperture whereby to define a first sensing chamber end wall, the first electrode facing the first side of the sheet;

mounting a second layer having a second electrode to a second side of the sheet and extending over the aperture whereby to define a second sensing chamber end wall in substantial overlying registration with the first layer, the second electrode facing the second side of the sheet, whereby the sheet and layers form a strip, and wherein the second electrode is mounted in opposing relationship a distance of less than about 500 microns from the first electrode;

providing an aperture in the strip to permit entry of sample into the sensing chamber;

providing a reagent capable of being reduced by hemoglobin, wherein the reagent is contained within the sensing chamber;

providing a red blood cell lysing agent, wherein the lysing agent is contained within the sensing chamber;

providing means for applying a positive potential to the first electrode; means for measuring a current generated by reaction of the reagent and hemoglobin;

providing means for analyzing the current to give a result, the result comprising a time required for substantial lysis of red blood cells or a derived final value for the current;

providing means for calculating a percentage of the reaction completed as a function of time based on the result of the analyzing step;

providing means for reversing the potential on the first electrode;

providing means for measuring a transient current; and providing means for determining a diffusion coefficient and a concentration of a reduced form of the reagent based on the transient current.

47. The method according to claim 46, further comprising the step of providing a vent in the strip to permit the escape of air displaced from the sensing chamber as sample fills the sensing chamber.

48. The method according to claim 46, wherein at least one of the electrodes comprises a noble metal.

49. The method according to claim 48, wherein the noble metal is selected from the group consisting of palladium, platinum, and silver.

50. The method according to claim 46, wherein the aperture is of a rectangular cross-section.

51. The method according to claim 46, wherein at least one of the electrodes is a sputter coated metal deposit.

52. The method according to claim 46, wherein the electrodes are adhered to the sheet.

53. The method according to claim 52, wherein the electrodes are adhered to the sheet by an adhesive.

54. The method according to claim 53, wherein the adhesive is selected from the group consisting of heat activated adhesive, pressure sensitive adhesive, heat cured adhesive, chemically cured adhesive, hot melt adhesive, and hot flow adhesive.

55. The method according to claim 46, further comprising the step of providing a buffer, the buffer being contained within the sensing chamber.

56. The method according to claim 55, further comprising the step of printing the buffer onto at least one wall of the sensing chamber.

57. The method according to claim 46, further comprising the step of printing the red blood cell lysing agent onto at least one wall of the sensing chamber.

58. The method according to claim 46, further comprising the step of printing the reagent onto at least one wall of the sensing chamber.

59. The method according to claim 46, further comprising the step of providing a support, the support contained within the sensing chamber.

60. The method according to claim 59, wherein the support is selected from the group consisting of mesh, fibrous filler, macroporous membrane, sintered powder, and combinations thereof.

61. The method according to claim 60, wherein the reagent is supported on or contained within the support.

62. The method according to claim 46, wherein at least the sheet or one of the layers comprises a polymeric material selected from the group consisting of polyester, polystyrene, polycarbonate, polyolefin, and mixtures thereof.

63. The method according to claim 46, wherein at least the sheet or one of the layers comprises polyethylene terephthalate.

64. The method according to claim 46, wherein the second electrode is mounted in opposing relationship a distance of less than about 150 microns from the first electrode.

65. The method according to claim 46, wherein the second electrode is mounted in opposing relationship a distance of less than about 150 microns and greater than about 50 microns from the first electrode.

66. The method according to claim 46, wherein the device may only be used for a single-test.

* * * * *